United States Patent [19]

Jordy et al.

[11] 4,287,171

[45] Sep. 1, 1981

[54] STORAGE STABLE QUICKLY ACTING TABLETS FOR COMBATTING VERTEBRATES PREPONDERANTLY IN UNDERGROUND STRUCTURES

[75] Inventors: Angelika Jordy, Bad Homburg; Wolfgang Kapp, Offenbach am Main, both of Fed. Rep. of Germany

[73] Assignee: Degesch GmbH, Frankfurt, Fed. Rep. of Germany

[21] Appl. No.: 38,226

[22] Filed: May 11, 1979

[30] Foreign Application Priority Data

Jun. 28, 1978 [DE] Fed. Rep. of Germany ....... 2825534

[51] Int. Cl.$^3$ ..................... A01M 13/00; B65D 75/26; A01N 59/26; A01M 25/00
[52] U.S. Cl. .................................. 424/29; 43/124; 43/125; 43/129; 43/131; 206/484; 206/484.2; 424/14; 424/16; 424/30; 424/128
[58] Field of Search ................. 43/124, 125, 129, 131; 424/17, 29, 128; 206/484, 484.2, 532, 538, 539; 426/126, 316, 415

[56] References Cited

U.S. PATENT DOCUMENTS

| | | | |
|---|---|---|---|
| 2,921,401 | 1/1960 | Kawamura | 43/131 |
| 3,032,915 | 5/1962 | Giroud-Abel | 43/131 |
| 3,094,805 | 6/1963 | Luck | 43/131 |
| 3,177,610 | 4/1965 | Smith | 43/131 |
| 3,223,231 | 12/1965 | Connolly | 206/47 |
| 3,466,789 | 9/1969 | Kare | 43/131 |
| 3,494,457 | 2/1970 | Titchenal | 206/484 |
| 3,556,816 | 1/1971 | Nughes | 426/126 |
| 3,605,321 | 9/1971 | Lazarus | 43/131 |
| 3,625,712 | 12/1971 | Wilson | 426/415 |
| 3,634,099 | 1/1972 | Wilson | 426/415 |
| 3,759,379 | 9/1973 | Wrede | 206/484 |
| 3,771,254 | 11/1973 | Scott et al. | 43/131 |
| 3,866,347 | 2/1975 | Schoom | 43/129 |
| 3,906,656 | 9/1975 | Burke et al. | 43/131 |
| 3,912,843 | 10/1975 | Brazier | 426/415 |
| 3,949,114 | 4/1976 | Viola et al. | 426/126 |
| 4,043,073 | 8/1977 | Basile | 43/124 |
| 4,048,361 | 9/1977 | Valyi | 426/415 |
| 4,057,667 | 11/1977 | Wiggins et al. | 426/415 |
| 4,058,632 | 11/1977 | Evans et al. | 426/126 |
| 4,107,362 | 8/1978 | Valyi | 426/415 |
| 4,135,622 | 1/1979 | Glick | 206/484 |
| 5,597,237 | 8/1971 | Nughes | 426/126 |

FOREIGN PATENT DOCUMENTS

| | | | |
|---|---|---|---|
| 1037427 | 8/1978 | Canada | 424/29 |
| 2414548 | 2/1975 | Fed. Rep. of Germany . | |
| 1026823 | 4/1966 | United Kingdom | 424/17 |
| 1036965 | 7/1966 | United Kingdom | 424/17 |
| 1300146 | 12/1972 | United Kingdom | 424/128 |
| 1506049 | 4/1978 | United Kingdom | 424/128 |
| 1507513 | 4/1978 | United Kingdom | 424/128 |

OTHER PUBLICATIONS

Lin et al. Chung-HuaNung Yeh Yen Chiu 1977 26(1): 72–80 Studies on the Effectiveness of Fumigants Celphos and Phostoxin Against Granary Insects and Their Effects on Seed Germination, Chem. Abstracts 87: 178989P (1977).

Hanlon Handbook of Package Engineering (1971) McGraw-Hill (TS 195H 35) pp. vii–ix, 1-1-1-28, 3-1-–3-9, 3-20-3-37, 3-44-3-47, 3-50-3-60, 8-1, 8-36-8⇌, 10-1-10-11, 13-1-13-8 16-20-16-23 index.

Kashi et al. Chem Abst. 88 #33171b (1978) of Pestic. Sci. 1977 8(5):492–496, Rapid Evaluation of Phosphine Permeability Through Various Flexible Films and Coated Fabrics.

Kuo et al. Storage of Rice Grain with Plastic Bag Package and Phostoxin Fumigation, National Science Council Monthly, vol. VI, No. 7:639–650 Jul. 1, 1978.

Proctor J. Stored Products Research 8(2):127–137 (1972) The Control of Insects in Exported Zambian Groundnuts Using Phosphine and Polyethylene Lined Sacks.

Leesch et al. "Fumigation of Shrink-Wrapped Pallets" J. Ga. Ento. Soc. 13(1):43–50.

Kuo et al., Chem. Abst. 90 #4599h (1979).

Leesch et al. Chem. Abstr. 88 #131980j (1978).

Vardell et al., Chem. Abstr. 80 #104824g (1974) of J. Econ. Entomol. 1973 665:1209–1210.

Proctor et al. C. A. 77 148498d (1972).

Greaves et al., Chem. Abstr. 87 #147042v (1977).

Chaudhry et al., Chem. Abstr. 86 #84732b (1977).

Chandurkar et al., Chem. Abstr. 79 #14439t (1973).

Kapp et al., Chem. Abstr. 84 #55339g (1976) of Ger.

Offen. 2,414,548, Oct. 20, 1975 (earlier published counterpart of Canada 1,037,427-8/29/78).

Highland et al., Cereal Foods World 24(1):19-21 Jan. 1979 "Phosphine and Methyl Bromide Fumigation of Commodities in Woven, Plastic or Paper Bags".

Vukovic Agrohemija v. 3-4:117-121 (1978) "Magnesium Phosphid as Fumigant".

*Primary Examiner*—Shep K. Rose
*Attorney, Agent, or Firm*—Cushman, Darby & Cushman

[57] ABSTRACT

Storage stable, quickly acting tablets for combatting vertebrates living preponderantly in underground structures are provided consisting of a mixture of commercial magnesium phosphide and at least one molding aid placed in a cavity depending on the size of the tablet in a water vapor impermeable, tear and break resistant film covered with a water vapor impermeable, non-tear resistant, non-break resistant film, the two films being sealed together tightly against water vapor and air at their edges.

5 Claims, 1 Drawing Figure

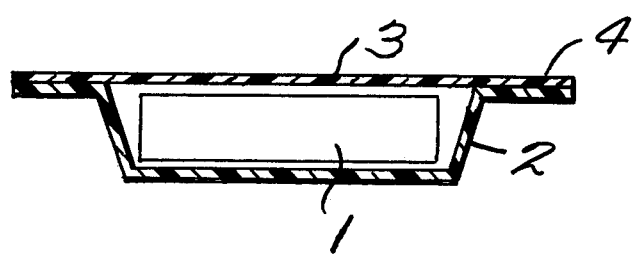

STORAGE STABLE QUICKLY ACTING TABLETS FOR COMBATTING VERTEBRATES PREPONDERANTLY IN UNDERGROUND STRUCTURES

BACKGROUND OF THE INVENTION

The invention is directed to a storage stable, quickly acting tablet for combatting vertebrates living preponderantly in underground structures, for example moles, voles, hamsters and foxes.

Customarily there are used for this purpose preparations of hydrophobized aluminum phosphide in the form of molded articles. A substantial disadvantage of these known agents is that they only develop phosphine slowly which frequently leads to the result that the animals (warned by the odor) are able to leave their buildings before a lethal concentration is reached. Furthermore, these known agents are not storage stable once the package is opened and the remaining contents exposed to the atmospheric moisture. Besides the known agents do not completely hydrolize so that there is not excluded the endangerment of the users or completely unconcerned people.

SUMMARY OF THE INVENTION

Therefore it is the purpose of the invention to produce a storage stable, quickly acting tablet for combatting vertebrates living preponderantiy in underground structures, the produce consisting essentially of a mixture of commercial magnesium phosphide and at least one mold assistant which tablet is individually placed in a cavity or recess depending on the size of the tablet in a water vapor and air impermeable, tear and break resistant film and covered with a water vapor and air impermeable, non-tear resistant and non-break resistant film, wherein the two films are sealed together (e.g., welded) at their edges tightly against water vapor and air. The tablets encased by the film are filled into cans from which they can be withdrawn individually.

Because of the exclusion of air and water vapor the tablets of the invention are practically of unlimited storage stability. However, if the tablet is broken then the non-tear and non-break resistant covering film also breaks through and the magnesium phosphide is exposed to the influence of air moisture or ground moisture.

The use of the tablet of the invention therefore is simple in conception and without danger. The user need only break it and introduce it together with the package into the openings of the structures to be gassed without the need to touch the magnesium phosphide. Subsequently the openings are covered for example with earth or another suitable material.

Under the action of air or ground moisture it very quickly develops phosphine (for example in a marmot animal structure about 500 ppm $PH_3$).

The tablets consist essentially of 40–90% preferably 70–80% of commercial magnesium phosphide and correspondingly 60–10%, preferably 30–20% of at least one molding assistant. As molding aids there are suited, for example, finely divided silica, brick dust, talcum, aluminum oxide and magnesium oxide.

Preferably, however, there are utilized water soluble molding assistants such as e.g., polyethylene oxide and sodium chloride.

Particularly preferred as the molding assistant is urea. Generally it is suitable if the molding assistants used are not toxic and neither have a characteristic odor nor form decomposition products having a characteristic odor.

The tablet is placed in a cavity or recess corresponding to its dimensions formed for example, by deep drawing of a tear and break resistant, water vapor and air impermeable film and covered with a tearable and breakable but water vapor and air impermeable film. The two films are welded together at their edges in a water vapor and air tight manner.

As tear resistant and break resistant films there are particularly suited deep drawable laminated films. Such laminated films can consist of for example a layer of a thermoplastic synthetic resin such as polypropylene, polyethylene, polyamide, e.g., polycaprolactam or poly(hexamethylene adipamide) or polyester, e.g., polyethylene terephthalate and an aluminum layer overcoating a heat sealing layer. As the non-tear resistant and non-break resistant, coating film, aluminum films coating a heat sealing layer are particularly suited.

The tablets of the invention can be produced in any desired size. Especially advantageous, however, are tablets having a weight between 2 and 50 grams, particularly about 5 to 20 grams, in a thickness between 2 and 10 mm, especially 3 to 5 mm and a diameter of 30 to 70 mm, especially between 40 and 60 mm.

BRIEF DESCRIPTION OF THE DRAWINGS

The single FIGURE of the drawing shows in schematic fashion and partially in section the tablet and container combination of the invention.

Referring more specifically to the drawing the magnesium phosphide tablet 1 is located in a cup shaped cavity of the tear and break resistant film 2 and is covered with a tearable and breakable film 3. The two films are tightly sealed together at their edges 4 against water vapor and air.

Unless otherwise indicated all parts and percentages are by weight.

The product can comprise, consist essentially of or consist of the materials set forth.

The production and use of the pellets of the invention is explained in the following examples.

DESCRIPTION OF THE PREFERRED EMBODIMENTS

EXAMPLE 1 (Production)

80 parts by weight of powdery commercial magnesium phosphide, particle size 3–600 microns having 39.5% inert constituents (essentially magnesium oxide) created in the manufacture were homogeneously mixed under the exclusion of air moisture by mechanical stirring with 20 parts by weight of urea (particle size 30–400 microns). The powder was subsequently pressed in a tablet press to molded articles having a diameter of 50 mm and a thickness of 3.8 mm.

The tablets were placed in the laminated film (polypropylene, aluminum, heat sealing layer, total thickness 82 microns), the covering film (aluminum, heat sealing layer, total thickness 25 microns) and sealed between two annular formed heat sealing plates during which the lower plate had a temperature of 90° C. and the upper plate a temperature of 150° C.

EXAMPLE 2 (Use)

An operation was carried out in a field strongly infested with hamsters. For this purpose 88 earth structures were charged with the tablets of the invention (1 tablet per structure opening). After the insertion straw and grass were stuffed into the holes and they were coated with earth. Each structure opening was marked and entered on a sketch. The subsequent check was taken after 24 hours. Since the digging up of about 0.5–1 meter deep structures was not possible, the action was judged positive at structures which were still closed, as negative at structures which were opened in the meantime. In order to ascertain the time span between bringing in the tablets and entrance of the effect the characterized structures were opened a trifle at intervals of 10 minutes and a wire hook inserted up to the living chamber which was immediately approached by the readily sensitive hamsters, so long as the gas had not acted sufficiently. The time span between insertion of the tablets and the occurrence of the action fluctuated between 20 and 30 minutes.

Of the 88 structures covered with the tablets of the invention only one structure was again opened. Accordingly the degree of effectiveness was about 99%. The action also occurs with relatively dry ground.

The entire disclosure of German priority application P 28 25 534.7 is hereby incorporated by reference.

What is claimed is:

1. A process for combatting vertebrate animals living in an underground structure having an opening therein comprising providing a packaged storage stable, quickly acting tablet for combatting said vertebrates, said package consisting essentially of a tablet which consists essentially of a mixture of commercial magnesium phosphide and a mold assistant located in a cavity in a first film which is water vapor and air impermeable, tear and break resistant, said cavity having an open top, and covering the cavity across the open surface thereof a second film which is water vapor and air impermeable, non-tear resistant and non-break resistant, the two films being sealed together at their edges tightly against water vapor and airs so that water vapor and air cannot reach the tablet in the cavity, breaking the tablet and the non-tear resistant, non-break resistant second film without touching the magnesium phosphide and introducing the package with the broken film and tablet into the opening of the underground structure in order to gas the underground structure.

2. A process according to claim 1 including the step of covering the opening after introducing the package.

3. A process according to claim 1 wherein the tablet contains 40–90% of commercial magnesium phosphide and 60–10% of mold assistant.

4. A process according to claim 3 wherein the mold assistant is water soluble.

5. A process according to claim 4 wherein the mold assistant is urea.

* * * * *